(12) United States Patent
Baek et al.

(10) Patent No.: US 9,067,022 B2
(45) Date of Patent: Jun. 30, 2015

(54) INJECTION AMOUNT MEASURING APPARATUS

(71) Applicant: Samsung Electronics Co., Ltd., Gyeonggi-do (KR)

(72) Inventors: In-Geol Baek, Gyeonggi-do (KR); Jae-Kyung Kwak, Gyeonggi-do (KR)

(73) Assignee: Samsung Electronics Co., Ltd. (KR)

( * ) Notice: Subject to any disclaimer, the term of this patent is extended or adjusted under 35 U.S.C. 154(b) by 84 days.

(21) Appl. No.: 13/918,320

(22) Filed: Jun. 14, 2013

(65) Prior Publication Data

US 2013/0336555 A1 Dec. 19, 2013

(30) Foreign Application Priority Data

Jun. 14, 2012 (KR) .......................... 10-2012-0063544

(51) Int. Cl.
*G06K 9/00* (2006.01)
*A61M 5/31* (2006.01)
*A61M 5/178* (2006.01)
*A61M 5/24* (2006.01)
*A61M 5/315* (2006.01)
*G06K 9/62* (2006.01)

(52) U.S. Cl.
CPC ................ *A61M 5/31* (2013.01); *A61M 5/178* (2013.01); *A61M 5/24* (2013.01); *A61M 5/31525* (2013.01); *A61M 2205/3306* (2013.01); *A61M 2205/3317* (2013.01); *A61M 2205/6054* (2013.01); *A61M 2205/6072* (2013.01); *G06K 9/6217* (2013.01)

(58) Field of Classification Search
None
See application file for complete search history.

(56) References Cited

U.S. PATENT DOCUMENTS

| 6,068,615 | A | 5/2000 | Brown et al. |
| 6,110,148 | A | 8/2000 | Brown et al. |
| 2011/0009812 | A1 | 1/2011 | Brown |
| 2012/0022458 | A1 | 1/2012 | Oh et al. |
| 2012/0053527 | A1 | 3/2012 | Cirillo et al. |
| 2014/0194825 | A1* | 7/2014 | Nielsen et al. ................ 604/189 |

FOREIGN PATENT DOCUMENTS

| KR | 1020120009814 | 2/2012 |
| WO | WO 2006/120182 | 11/2006 |
| WO | WO 2011/117212 | 9/2011 |
| WO | WO 2013/004843 | 1/2013 |
| WO | WO 2013/004844 | 1/2013 |
| WO | WO 2013/010886 | 1/2013 |

OTHER PUBLICATIONS

Optical Mouse Cam; Optical mouse camera—Bidouille.org, Oct. 7, 2010.

* cited by examiner

*Primary Examiner* — Nirav G Patel
(74) *Attorney, Agent, or Firm* — The Farrell Law Firm, P.C.

(57) ABSTRACT

An injection amount measuring apparatus for a syringe indicated with injection amount absolute value information is provided. The injection amount measuring apparatus includes an injection amount absolute value information extracting unit configured to extract the injection amount absolute value information; a control unit configured to analyze the extracted injection amount absolute value information to determine injection amount information for an injection amount to be injected from the syringe; and a storage unit configured to store the injection amount information.

9 Claims, 4 Drawing Sheets

| 701 | 702 |
|---|---|
| <INJECTION TIME> | <INJECTION AMOUNT> |
| 2012. 3. 20. AM 5:27 | 8 |
| 2012. 3. 20. AM 11:40 | 12 |
| 2012. 3. 20. PM 5:20 | 30 |
| 2012. 3. 21. AM 8:30 | 14 |
| | 64 — 703 |

FIG.6

INJECTION AMOUNT MEASURING APPARATUS

PRIORITY

This application claims priority under 35 U.S.C. §119(a) to Korean Application Serial No. 10-2012-0063544, which was filed in the Korean Intellectual Property Office on Jun. 14, 2012, the entire content of which is incorporated herein by reference.

BACKGROUND OF THE INVENTION

1. Field of the Invention

The present invention relates generally to an injection amount measuring apparatus, and more particularly, to an injection amount measuring apparatus which is capable of sensing an input of an injection button of a syringe and an injection amount without direct electric or mechanical contact.

2. Description of the Related Art

The number of diabetic patients has been increasing, and hence insulin syringes, which are capable of being carried by a diabetic patient such that the diabetic patient can inject himself or herself with insulin, are being further developed. Conventionally, pen type insulin syringes have become widely available in order to maximize a user's convenience. An insulin pen is configured such that an injection amount can be determined by rotating a knob where injection amounts are indicated, and as a button arranged at a terminal end of the insulin pen is compressed, the insulin can be injected in the determined injection amount.

A diabetic patient must record an injection amount of insulin each time when injecting the insulin. This is because when the insulin accumulated in the diabetic patient is an excessively large quantity or an excessively small quantity, it may be harmful to the diabetic patient and even fatal. In addition, a medical attendant may determine and diagnose the disease state of the patient based on the cumulative injection amount of insulin or injection amount information.

However, with the insulin syringes which have been available up to now, the user must directly prepare injection amount information, such as a cumulative injection amount, injection time, and an injected amount at each injection time. When the user does not recognize the injection amount information, it may be harmful to the patient. Accordingly, there is a need to develop an apparatus which is capable of automatically gathering and managing various information items regarding the injection amount even if the user may not recognize the injection amount.

SUMMARY OF THE INVENTION

Accordingly, the present invention has been made to address the problems and disadvantages described above, and to provide at least the advantages described below. Accordingly, an aspect of the present invention provides an injection amount measuring device which is capable of measuring an absolute value of an injection amount to manage injection amount information.

In accordance with an aspect of the present invention, an injection amount measuring apparatus for a syringe indicated with injection amount absolute value information is provided. The injection amount measuring apparatus includes an injection amount absolute value information extracting unit configured to extract the injection amount absolute value information; a control unit configured to analyze the extracted injection amount absolute value information to determine injection amount information for an injection amount to be injected from the syringe; and a storage unit configured to store the injection amount information.

In accordance with another aspect of the present invention, a pen type syringe for injecting insulin is provided. The pen type syringe includes a number sleeve indicated with plural numbers for indicating an amount of insulin to be injected; and an injection amount adjusting unit for adjusting the amount of insulin to be injected. The number sleeve further includes preset patterns that correspond to the plural numbers.

BRIEF DESCRIPTION OF THE DRAWINGS

The above and other aspects, features, and advantages of the present invention will be more apparent from the following detailed description taken in conjunction with the accompanying drawings, in which:

FIG. 6 is an embodiment of injection amount information according to an embodiment of the present invention.

DETAILED DESCRIPTION OF EMBODIMENTS OF THE PRESENT INVENTION

Figure 1:
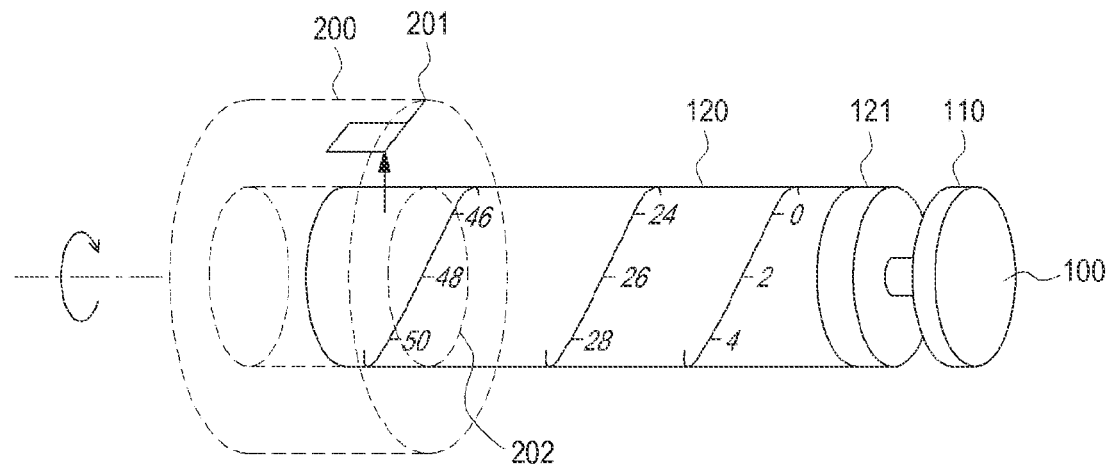
FIG. 1 is a conceptual view illustrating a syringe and an injection amount measuring apparatus according to an embodiment of the present invention.

Hereinafter, various embodiments of the present invention will be described with reference to the accompanying drawings. In the following description, the same elements will be designated by the same reference numerals if possible although they are shown in different drawings. Further, in the following description of the present invention, a detailed description of known functions and configurations incorporated herein will be omitted when it may make the subject matter of the present invention unclear.

According to various embodiments of the present invention, an injection amount measuring apparatus is provided that is capable of measuring an absolute value of an injection amount and managing injection amount information. The inventive injection amount measuring apparatus avoids an injection amount measuring error which may be caused in a mechanical configuration that measures a number of rotations of a knob when measuring an absolute value of an injection amount.

FIG. 1 is a conceptual view illustrating a syringe and an injection amount measuring apparatus according to an embodiment of the present invention. As illustrated in FIG. 1, the injection amount measuring apparatus 200 may be implemented as a device attached to a part of a syringe 100. The injection amount measuring apparatus 200 may be detachable from the part of the syringe 100. More specifically, the injection amount measuring apparatus 200 includes an opening 202, into which the syringe 100 is introduced, and the syringe 100 is introduced into and attached to the opening 202. Meanwhile, the construction, in which the syringe 100 is introduced into and attached to the opening 202 of the injection amount measuring apparatus 200, is only illustrative, and various modified embodiments may be made by changing the design of the above-mentioned construction. For example, a construction in which the injection amount measuring apparatus 200 is implemented in a cuff type and attached to the syringe 100 by wrapping the syringe 100 may be provided. That is, the scope of the present invention is not limited by the configuration of the injection amount measuring apparatus 200, or a method of attaching or detaching the injection amount measuring apparatus 200 and the syringe 100.

The syringe 100 includes an injection button 110, a number sleeve 120, and an injection amount adjusting unit 121. The syringe 100 contains insulin to be injected into a user, and although not illustrated, may include a pen type syringe to be used when giving an injection to the user. The user presses the injection button 110 to inject the insulin within the syringe 100. More specifically, as the injection button 110 compresses the insulin, the insulin can be injected. Although not illustrated, the syringe 100 may further include an insulin storage unit for storing insulin.

The number sleeve 120 is indicated with plural numbers and markings which correspond to the numbers, respectively. The plural numbers of the number sleeve 120 may be indicated to be spirally increased on the outer circumferential surface of the syringe 100. Each of the plural numbers indicated on the number sleeve 120 indicates an amount of insulin to be injected.

The user adjusts the amount of insulin to be injected by rotating the injection amount adjusting unit 121. The user determines the amount of insulin to be injected by rotating the injection amount adjusting unit 121 while confirming the numbers and markings of the number sleeve 120.

An injection amount absolute value information extracting unit 201 extracts information for an absolute value of an injection amount (the information may also be referred to as "injection amount absolute value information"). For example, if the user determines the amount of insulin to be injected as "48", the user rotates the injection amount adjusting unit 121 to adjust the injection amount to "48". The injection amount absolute value information extracting unit 201 extracts the information for the absolute value of the injection amount, "48". The configuration of the injection amount absolute value information extracting unit 201 for extracting the injection amount absolute value information will be described in more detail below.

The injection amount absolute value information extracted by the injection amount absolute information extracting unit 201 may be stored in a storage unit (not illustrated). The user may recognize injection amount related information, such as a cumulative injection amount, or injection performed time and an injection amount corresponding to the time, by confirming the injection amount absolute value information stored in the storage unit (not illustrated).

Figure 2:
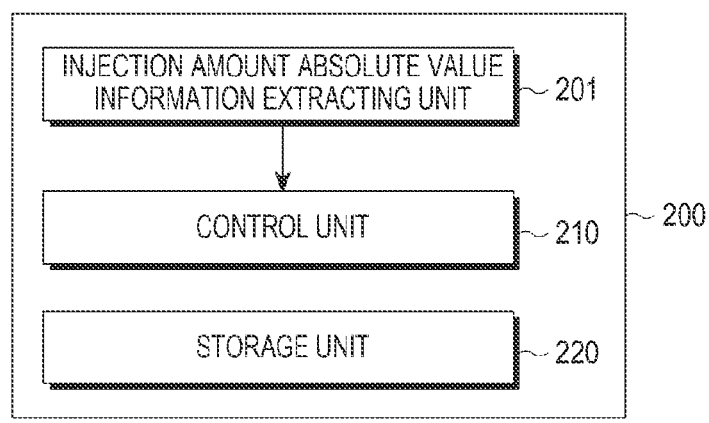
FIG. 2 is a block diagram of an injection amount measuring apparatus according to an embodiment of the present invention.

FIG. 2 is a block diagram of an injection amount measuring apparatus according to an embodiment of the present invention. As illustrated in FIG. 2, the injection amount measuring apparatus injection amount measuring apparatus 200 includes the injection amount absolute value information extracting unit 201, a control unit 210, and a storage unit 220.

The injection amount absolute value information extracting unit 201 extracts information for the absolute value of the determined injection amount of insulin. The injection amount absolute value information extracting unit extracts the injection amount absolute value information based on, for example, an Optical Character Recognition (OCR) technology. Meanwhile, the extraction of injection amount absolute information as described above is merely an illustrative example, and a person ordinarily skilled in the art may easily make a design change for the configuration capable of extracting injection amount absolute value information. The scope of the present invention is not limited by the process of extracting the injection amount absolute value information.

The control unit 202 receives an input of injection amount absolute value information, and controls the input injection amount information to be converted by a predetermined method to be stored in the storage unit 203. For example, the control unit 202 may perform a control such that the injection amount absolute value information and the cumulative injection amount absolute value information are stored in the storage unit 203 simultaneously. Also, the control unit 202 may perform a control such that the injection performed time and the injection amount absolute value information are stored in the storage unit 203 simultaneously.

As described above, the injection amount measuring apparatus 200 may store not only the injection amount but also information related to the cumulative injection amount or the time when injecting. As a result, a patient or a medical attendant may easily manage information related to the amount of insulin injected into the patient.

Figure 3:
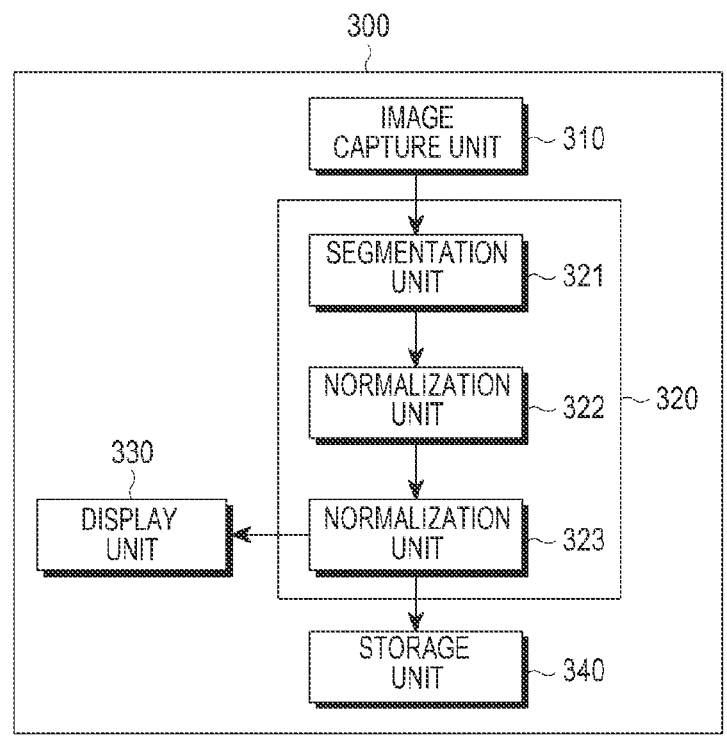
FIG. 3 is a block diagram of an injection amount measuring apparatus that extracts injection amount absolute value information based on Optical Character Recognition (OCR) according to an embodiment of the present invention.

FIG. 3 is a block diagram of an injection amount measuring apparatus that extracts injection amount absolute value information based on OCR according to an embodiment of the present invention.

As illustrated in FIG. 3, the injection amount measuring apparatus 300 includes an image capture unit 310, a control unit 320, a display unit 330, and a storage unit 340.

The image capture unit 310 captures an image for optical information of an injection amount absolute value. For example, the image capture unit 310 may capture the numbers indicated on the number sleeve, or patterns indicated separately from the numbers on the number sleeve. More specifically, the image capture unit 310 captures the number or pattern corresponding to a determined injection amount on the number sleeve 120. The image capture unit 310 may be implemented by a camera module that is a Charge Coupled Device (CCD) or a Complementary Metal Oxide Semiconductor (CMOS). The number or pattern captured by the image capture unit 310 is output to the control unit 320.

A segmentation unit 321 segments the numbers or patterns captured by the image capture unit 310. A normalization unit 322 normalizes each of the segmented number areas, and a recognition unit 323 recognizes a normalized area to recognize what the corresponding number is. Meanwhile, the method of segmenting, normalizing and then recognizing numbers is merely an embodiment of OCR technologies, and the present invention may recognize numbers or patterns based on various OCR technologies other than the above-mentioned OCR technology. The control unit 320 may be implemented in a form of a central computing processing system, an IC chip or a micro-computer that performs a predetermined calculation.

The number-recognized result is displayed on the display unit 330. The display unit 330 displays a recognized injection amount. Based on this, the user determines whether a correct injection amount is recognized or not. The display unit 330 may be implemented by an LCD module.

In addition, the number-recognized result may be stored in the storage unit 340. Meanwhile, when the injection amount information based on the recognized number is stored in the storage unit 340, the control unit 320 may performs a control such that the injection amount information and the information related to the time at the injection timing are stored simultaneously. The display unit 330 displays at least one of the injection amount information, the information related to the time at the injection timing, and the cumulative injection amount.

Figure 4:
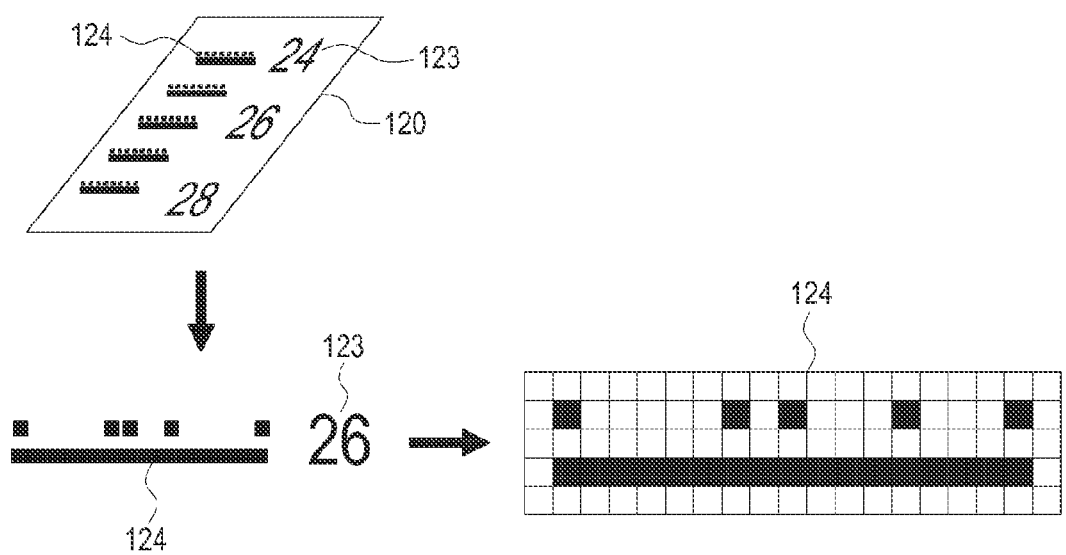
FIG. 4 is a conceptual view for describing a process of measuring an injection amount according to an embodiment.

FIG. 4 is a conceptual view for describing a process of measuring an injection amount according to an embodiment of the present invention. The number sleeve 120 includes plural numbers and patterns that correspond to the numbers, respectively. As described above, each of the numbers indicate an amount of insulin to be injected. In addition, a pattern is indicated adjacent to each number, indicating the amount of insulin to be injected as a preset form. For example, the user may determine the injection amount as "24". A pattern, for example, indicated by reference numeral 124, which corresponds to an injection amount number "24" indicated by reference numeral 123, is appointed as a preset format which may mean "24".

The control unit 320 recognizes the injection number 123 based on various OCR technologies including the abovementioned OCR technologies. Alternatively, the control unit 320 may recognize the pattern 124 based on the OCR technologies. As illustrated in FIG. 4, each of the patterns may take a form in which some of plural grids are indicated. The control unit 320 distinguishes indicated grids and non-indicated grids among plural grids of a pattern. According to the distinguished result, the control unit 320 recognizes a pattern and extracts injection amount information. For example, as illustrated in FIG. 4, a pattern, in which the first, seventh, ninth, thirteenth and seventeenth grids are indicated, may be preset as meaning an injection amount "26". From the captured pattern, the control unit 320 determines the information that the first, seventh, ninth, thirteenth and seventeenth grids are indicated. In addition, control unit 320 determines that the pattern in which the first, seventh, ninth, thirteenth and seventeenth grids are indicated means the injection amount "26", and hence determines that the determined injection amount is "26".

Figure 5:
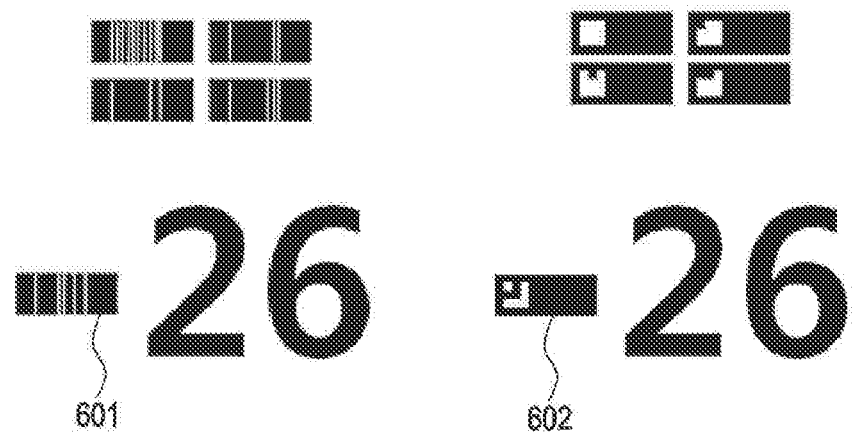
FIG. 5 is a conceptual view for describing a process of measuring an injection amount based on RF technology according to another embodiment of the present invention.

FIG. 5 is a conceptual view for describing a process of measuring an injection amount based on an RF technology according to another embodiment of the present invention. As illustrated in FIG. 5, the inventive number sleeve 120 may be indicated with plural numbers and RF tags 601 and 602 that correspond to the plural numbers, respectively. Here, the RF tag 601 is a vertical bar code, and the RF tag 602 depicts a two-dimensional bar code. Each of the numbers indicate an amount of insulin to be injected as described above. In addition, a bar code indicated adjacent to each of the numbers indicates a preset amount of insulin to be injected. For example, the user may determine an injection amount as "26". The bar code 601 or 602 corresponding to the number of the injection amount is appointed as a preset format which means "26".

FIG. 6 is an embodiment of injection amount information according to an embodiment of the present invention. As illustrated in FIG. 6, injection amount information includes time information related to injected timings 701, information related to an injection amount for each timing 702 and information related to a cumulative injection amount 703. The injection amount measuring apparatus according to an embodiment of the present invention displays injection amount information as illustrated in FIG. 6 on a display means. Alternatively, the injection amount measuring apparatus may store the injection amount information as illustrated in FIG. 6 on a storage means and then may read out and confirm the injection amount information. By confirming the information, the user determines the amount of insulin and the timings injected by the user thereof, and then determines the amount of insulin and the timing to be injected. In addition, a medical attendant may determine the injection amount information of a patient and easily determine a condition of the patient.

While the present invention has been shown and described with reference to certain embodiments thereof, it will be understood by those skilled in the art that various changes in form and details may be made therein without departing from the spirit and scope of the present invention as defined by the appended claims.

What is claimed is:

1. An injection amount measuring apparatus for a syringe indicated with injection amount absolute value information, the apparatus comprising:
    an injection amount absolute value information extracting unit configured to extract the injection amount absolute value information;
    a control unit configured to analyze the extracted injection amount absolute value information to determine injection amount information for an injection amount to be injected from the syringe; and
    a storage unit configured to store the injection amount information,
    wherein the injection amount absolute value information extracting unit captures an image of the injection amount absolute value information, and the control unit recognizes the injection amount based on the captured injection amount absolute value information using Optical Character Recognition (OCR) technology.

2. The apparatus of claim 1, wherein the injection amount absolute value information includes at least one of a number corresponding to the injection amount and a pattern preset to correspond to the injection amount.

3. The apparatus of claim 2, wherein when the control unit recognizes the number corresponding to the injection amount, the number is segmented, and the segmented number is normalized and recognized, according to the OCR technology.

4. The apparatus of claim 2, wherein the pattern includes at least one grid.

5. The apparatus of claim 4, wherein when the control unit recognizes the pattern corresponding to the injection amount, the control unit differentiates indicated grids and non-indicated grids among grids in the pattern, and analyzes the coordinates of the indicated grids to recognize the injection amount absolute value.

6. The apparatus of claim 1, wherein the control unit performs a control such that the time of injection by the syringe is stored in the storage unit.

7. The apparatus of claim 1, wherein the control unit performs a control such that the injection amount information is measured plural times, and cumulative injection amount information is calculated and stored in the storage unit.

8. The apparatus of claim 1, further comprising:
    a display unit for displaying the injection amount information.

9. The apparatus of claim 1, further comprising:
    an opening, into which the syringe is introduced, such that the syringe is attached to the injection amount measuring apparatus.

* * * * *